United States Patent [19]

Pollet et al.

[11] Patent Number: 4,727,017

[45] Date of Patent: Feb. 23, 1988

[54] SUBSTITUTED TRIAZOLOPYRIMIDINES AND THEIR USE IN LIGHT-SENSITIVE PHOTOGRAPHIC ELEMENTS

[75] Inventors: Robert J. Pollet, Vremde; Antoon L. Vandenberghe, Hove; Hendrik E. Kokelenberg, Merksem; Piet Kok, Ghent, all of Belgium

[73] Assignee: Agfa-Gevaert, N.V., Mortsel, Belgium

[21] Appl. No.: 823,948

[22] Filed: Jan. 29, 1986

[30] Foreign Application Priority Data

Feb. 4, 1985 [EP] European Pat. Off. ..... EP 85101126

[51] Int. Cl.$^4$ .............................................. G03C 1/34
[52] U.S. Cl. .................................. 430/611; 430/615; 430/264; 430/949
[58] Field of Search ................ 430/264, 949, 611, 615

[56] References Cited

U.S. PATENT DOCUMENTS 4,542,094 9/1985 Koshizuka et al. ................ 430/615

FOREIGN PATENT DOCUMENTS 1500278 2/1978 United Kingdom .

Primary Examiner—Won H. Louie
Attorney, Agent, or Firm—A. W. Breiner

[57] ABSTRACT

Photographic element comprising a support and a silver halide emulsion layer comprising in said emulsion layer and/or in a water-permeable layer coated at the same side of the support as said emulsion layer a compound corresponding to the following general formula:

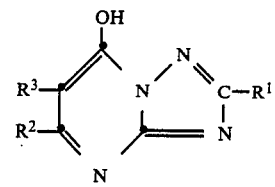

wherein:

each of $R^1$, $R^2$, and $R^3$, which may be the same or different, can represent hydrogen, $C_1$–$C_8$alkyl, or $Alk_1$ - X - $Alk_2$ - Y -, wherein: $Alk_1$ is $C_1$–$C_8$alkyl, which may be substituted, X is —O— or —S—, $Alk_2$ is $C_1$–$C_8$alkylene, which may be substituted, and Y is a single bond, —O—, —S—, —CONH—, —SO$_2$NH—, or —NHCONH—, $R^3$ can alternatively represent $C_1$–$C_8$alkyl-thio, the $C_1$–$C_8$alkyl group of which can be substituted, at least one of $R^1$, $R^2$, and $R^3$, however, being other than hydrogen and other than $C_1$–$C_8$alkyl.

The invention disclosed includes compounds per se, which correspond to said general formula.

7 Claims, No Drawings

SUBSTITUTED TRIAZOLOPYRIMIDINES AND THEIR USE IN LIGHT-SENSITIVE PHOTOGRAPHIC ELEMENTS

The present invention relates to improved photographic elements comprising light-sensitive silver halide emulsions containing substituted triazolopyrimidines.

It is well known that photographic elements comprising light-sensitive gelatin silver halide emulsion layers are subject to fogging. Fogging in general and chemical fogging in particular can be defined as the formation of a uniform deposit of silver on development. The formation of fog depends on many variables such as the nature of the silver halide emulsions, their age, the conditions of storage, the development conditions, etc. Anyway, fog adversely influences the image quality. The formation of fog tends to be more extensive as the time of storage and the temperature and relative humidity of the atmosphere in which the emulsions are stored, increase.

Additives to the photographic material known as stabilizers or antifoggants protect the light-sensitive silver halide emulsions against formation and growth of fog particularly in highly sensitive emulsions and in emulsions which are to be stored in conditions of high temperature and humidity as exist e.g. in tropical countries.

It is well known to use compounds of the triazolopyrimidine type (azaindolizines) as stabilizers for light-sensitive silver halide emulsions.

It is also known to use certain compounds of the triazolopyrimidine type as substitutes for cadmium salts, which have been used successfully in high contrast silver halide lith emulsions to improve their sensitivity and contrast. Regretfully, cadmium salts are ecologically harmful.

Several attempts have been made to find modified triazolopyrimidine stabilizers, which stabilize light-sensitive silver halide emulsions in extreme storage circumstances and at the same time do not decrease their sensitivity. For instance the U.S. patent specification No. 2,566,659, the Dutch patent application No. 6501053, and the European patent application No. 0 096 561 describe the use of thioether-substituted triazolopyrimidines in light-sensitive silver halide emulsions to protect them against the growth of chemical fog during storage. The U.K. patent specification No. 1,203,757 describes the use of iodo-substituted triazolopyrimidines and U.K. Patent specification No. 1,209,146 the use of amino-substituted triazolopyrimidines for the same purpose. Other modified triazolopyrimidines were claimed to have a stabilizing effect on silver halide emulsions including lith emulsions. For instance the Japanese Patent application No 75-39537 teaches the use of isothioureido-substituted triazolopyrimidines and the U.K. Patent specification No. 1,500,278 describes the use of carboxymethylthio-substituted triazolopyrimidines as substitutes for cadmium salts in lith emulsions.

Nevertheless there is still a need of improving the stabilization of light-sensitive silver halide emulsions whilst maintaining their sensitivity.

There also remains a need to provide compounds that replace the ecologically harmful cadmium salts formerly used in lith emulsions to improve their photographic characteristics, especially their gradation.

It has now been found that substituted triazolopyrimidines as defined hereinafter can be used for these purposes.

Accordingly the present invention provides a photographic element comprising a support and at least one light-sensitive silver halide emulsion layer and comprising in said emulsion layer and/or in at least one water-permeable hydrophilic colloid layer coated at the same side of the support as said emulsion layer at least one 7-hydroxy-s-triazolo[1,5-a]-pyrimidine compound corresponding to the following general formula:

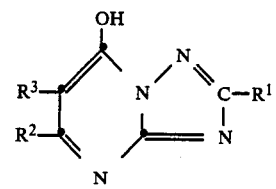

wherein:
each of $R^1$, $R^2$, and $R^3$, which may be the same or different, can represent:
  hydrogen,
  a $C_1$–$C_8$ alkyl group, e.g. methyl, or
  an $Alk_1$—X—$Alk_2$—Y— group, wherein
    $Alk_1$ represents a $C_1$–$C_8$alkyl group e.g. methyl, ethyl, or octyl, or a substituted $C_1$–$C_8$alkyl group e.g. $C_1$–$C_8$Alkylsubstituted with hydroxy, carboxy, acetoxy, phenyl $C_1$–$C_8$alkyl-thio such as methylthio or ethylthio, $C_1$–$C_8$alkyloxy such as methoxy, hydroxy-$C_1$–$C_8$Alkylthio such as 2-hydroxyethylthio, or hydroxy-$C_1$–$C_8$alkyloxy,
    X represents —O— or —S—,
    $Alk_2$ represents a $C_1$–$C_8$alkylene group e.g. methylene or ethylene, or a substituted $C_1$–$C_8$alkylene group e.g. $C_1$–$C_8$alkylene substituted with carboxy or carboxymethyl, and
    Y represents a single bond, —O—, —S—, —CONH—, —SO$_2$NH—, or —NHCONH—,
  $R^3$ can alternatively represent a $C_1$–$C_8$alkyl-thio group or a $C_1$–$C_8$Alkyl-thio group, the $C_1$–$C_8$Alkyl of which can be substituted with hydroxy, carboxy, acetoxy, phenyl, $C_1$–$C_8$alkylthio, $C_1$–$C_8$Alkyloxy, hydroxy-$C_1$–$C_8$Alkylthio, or hydroxy-$C_1$–$C_8$alkyloxy,
  at least one of $R^1$, $R^2$, and $R^3$, however, being other than hydrogen and other than $C_1$–$C_8$alkyl.

It has been established that 7-hydroxy-s-triazolo-[1,5-a]-pyrimidines corresponding to the above general formula are particularly good stabilizers and antifoggants for both colour and black-and white photographic light-sensitive silver halide emulsions and maintain their sensitivity.

It has also been found that said 7-hydroxy-s-triazolo-[1,5-a]-pyrimidines corresponding to the above general formula improve the photographic characteristics of lith emulsions. They actually increase their gradation and sharpen the toe of the characteristic curve as is very much desirable in the case of lith emulsions. Unlike cadmium salts they do not harm the environment and thus are interesting substitutes for these heavy metal salts.

Representatives of said 7-hydroxy-s-triazolo-[1,5-a]-pyrimidine compounds corresponding to the above general formula that can be used in accordance with the present invention are listed in the following Table 1, the symbols used therein referring to the above general formula.

into the specific $R^1$, $R^2$, and/or $R^3$ substituents of the compounds of the invention.

TABLE 1

| Compound | $R^1$ | $R^2$ | $R^3$ |
|---|---|---|---|
| 1 | —$CH_2$—O—$CH_3$ | —$CH_3$ | —H |
| 2 | —$CH_2$—S—$CH_3$ | —$CH_3$ | —H |
| 3 | —$CH_2$—S—$(CH_2)_7$—$CH_3$ | —$CH_3$ | —H |
| 4 | —$CH_2$—S—$CH_2COOH$ | —$CH_3$ | —H |
| 5 | —$CH_2$—S—$CH_2CH_2OH$ | —$CH_3$ | —H |
| 6 | —$CH_2$—S—$CH_2CH_2$—S—$C_2H_5$ | —$CH_3$ | —H |
| 7 | —$CH_2$—S—$CH_2CH_2$—S—$CH_2CH_2OH$ | —$CH_3$ | —H |
| 8 | —$CH_2$—S—$CH_2$—$C_6H_5$ | —$CH_3$ | —H |
| 9 | —$CH_2CH_2$—S—$CH_3$ | —$CH_3$ | —H |
| 10 | —S—$CH_2CH_2$—S—$C_2H_5$ | —$CH_3$ | —H |
| 11 | —S—$CH_2CH_2$—S—$CH_2CH_2OH$ | —$CH_3$ | —H |
| 12 | —NHCO—$CH_2$—S—$CH_3$ | —$CH_3$ | —H |
| 13 | —NHCO—$CH_2$—O—$CH_3$ | —$CH_3$ | —H |
| 14 | —H | —$CH_2$—O—$CH_3$ | —H |
| 15 | —H | —$CH_2$—S—$CH_3$ | —H |
| 16 | —H | —$CH_2$—S—$CH_2COOH$ | —H |
| 17 | —H | —$CH_2$—S—$CH_2CH_2O$—CO—$CH_3$ | —H |
| 18 | —H | —$CH_2$—S—$CH_2CH_2OH$ | —H |
| 19 | —H | —$CH_2$—S—$CH_2$—$C_6H_5$ | —H |
| 20 | —H | —$CH_2$—S—$CH_2CH_2$—S—$C_2H_5$ | —H |
| 21 | —$CH_2$—S—$CH_3$ | —$CH_2$—S—$CH_3$ | —H |
| 22 | —H | —$CH_3$ | —S—$CH_2$—$C_6H_5$ |
| 23 | —H | —$CH_3$ | —S—$CH_2$—COOH |
| 24 | —H | —$CH_3$ | —S—$CH_2$—$CH_2O$—CO—$CH_3$ |
| 25 | —H | —$CH_3$ | —S—$CH_2$—$CH_2OH$ |
| 26 | —H | —$CH_3$ | —S—$CH_2$—CHOH—$CH_2OH$ |
| 27 | —H | —$CH_3$ | —S—$CH_2$—$CH_2$—S—$CH_2$—$CH_2OH$ |
| 28 | —H | —$CH_3$ | —$CH_2$—S—$CH_3$ |
| 29 | —H | —$CH_3$ | —$CH_2$—S—$CH_2$—COOH |
| 30 | —H | —$CH_3$ | —$CH_2$—S—$CH_2$—$CH_2OH$ |
| 31 | —H | —$CH_3$ | —NHCO—$CH_2$—S—$CH_3$ |
| 32 | —H | —$CH_3$ | —NHCO—$CH_2$—S—$CH_2$—COOH |
| 33 | —H | —$CH_3$ | —NHCO—CH—S—$(CH_2)_3$—$CH_3$<br>               \|<br>               $CH_2$—COOH |
| 34 | —H | —$CH_3$ | —NHCO—$CH_2$—O—$CH_3$ |
| 35 | —H | —$CH_3$ | —NHCO—$CH_2$—O—$CH_2$—COOH |

7-Hydroxy-s-triazolo-[1,5-a]-pyrimidine compounds having the above general formula are believed to be new compounds and the present invention also includes such compounds per se.

The 7-hydroxy-s-triazolo-[1,5-a]-pyrimidine compounds corresponding to the above general formula can be prepared by techniques described by G. Fischer in Journal füR Signalaufzeichnungsmaterialien 1, 33–42 (1973). They can be prepared by condensation of a β-ketoester or of a substituted β-ketoester with a 5-amino-1,2,4-triazole according to the following reaction scheme:

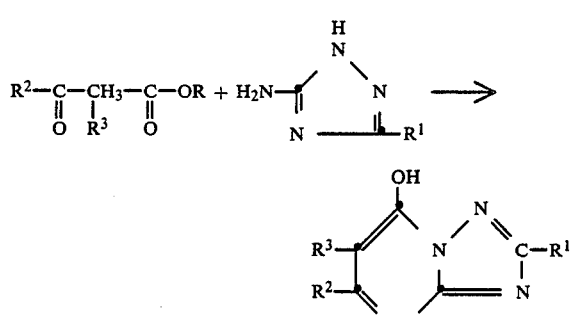

They can be obtained also by conversion of appropriate substituents such as e.g. a mercapto group or an amino group standing on the 2-, 5-, and/or 6-position of a 7-hydroxy-s-triazolo-[1,5-a]-pyrimidine ring system into the specific $R^1$, $R^2$, and/or $R^3$ substituents of the compounds of the invention.

According to these methods the compounds of the invention can be prepared very simply and very economically.

A description of the synthesis of some of the compounds identified in Table 1 is given hereinafter by way of example. The synthesis of other compounds identified in Table 1 as well as of compounds not identified in Table 1 but corresponding to the above general formula can easily be derived from the syntheses described hereinafter.

Preparation 1: Compound 1

An amount of 21.8 g (0.17 mol) of 3-methoxymethyl-5-amino-1,2,4-triazole melting at 100° C. and prepared from aminoguanidinium hydrogen carbonate and methoxyacetic acid in toluene as described in the U.K. patent specification No. 765,728 and 32.5 g (0.28 mol) of methyl acetoacetate was refluxed for 4 h in 50 ml of acetic acid. A mixture consisting of methanol, water, and acetic acid (25 ml) was distilled off. The remaining reaction mixture was stirred with 50 ml of ethanol, filtered with suction, and rinsed with ethanol.

Yield: 11.5 g (35%) of Compound 1. Melting point: >265° C.

Preparation 2: Compound 2

Compound 2 was prepared analogously to Compound 1 as described above, but from 3-methylthiomethyl-5-amino-1,2,4-triazole melting at 125° C. and methyl acetoacetate in acetic acid.

Yield: (42%). Melting point: 243° C.

Preparation 3: Compound 4

(a) 2-Mercaptomethyl-5-methyl-7-hydroxy-s-triazolo-[1,5-a]-pyrimidine was prepared by first hydrolysing the corresponding thiouronium salt, as described in the U.S. patent specification No. 2,835,581, in boiling aqueous sodium hydroxide under nitrogen atmosphere and then acidifying.

Yield: (75%). Melting point: 215° C.

(b) A solution of 23.3 g (0.2 mol) of the sodium salt of chloroacetic acid in 150 ml of water was added dropwise under nitrogen atmosphere to a solution of 39.2 g (0.2 mol) of compound (a), prepared as described above, in 80 ml (0.4 mol) of 5 N sodium hydroxide. After having been stirred for 6 h at room temperature, the reaction mixture was filtered. The filtrate was acidified with concentrated hydrochloric acid. The precipitate was filtered with suction and rinsed with water and methanol.

Yield: 37.5 g (74%) of 2-carboxymethylthiomethyl-5-methyl-7-hydroxy-s-triazolo-[1,5-a]-pyrimidine(Compound 4). Melting point: >265° C.

Preparation 4: Compound 6

17.4 g (0.08 mol) of 3-[2-(ethylthio)-ethylthiomethyl]-5-amino-1,2,4-triazole melting at about 80° C. and 13.9 g (0.12 mol) of methyl acetoacetate were refluxed for 4 h in 30 ml of acetic acid. The precipitate was filtered with suction and rinsed with ethanol.

Yield: 13.5 g (59%) of Compound 6. Melting point: about 165° C.

Preparation 5: Compound 9

Compound 9 was prepared analogously to Compound 1 as described above, but from 3-[2-(methylthio)-ethyl]-5-amino-1,2,4-triazole melting at about 110° C. and methyl acetoacetate in acetic acid.

Yield: (69%). Melting point: 222° C.

Preparation 6: Compound 10

Compound 10 was prepared analogously to Compound 1.

Yield: (30%). Melting point: 168° C.

Preparation 7: Compound 14

Compound 14 was prepared analogously to Compound 1 as described above, but from ethyl 4-methoxyacetoacetate boiling at 55°–60° C./5 mm and prepared as described in Journal of Organic Chemistry 43, 2087 (1978).

Yield: (75%). Melting point: about 265° C.

Preparation 8: Compound 15

Compound 15 was prepared analogously to Compound 6 as described above, but from 4-(methylthio)acetoacetic acid methyl ester boiling at 78°–79° C./1.5 mm.

Yield: (73%). Melting point: 215° C.

Preparation 9: Compound 17

Compound 17 was prepared analogously to Compound 1 as described above, but from 4-(2-acetoxy-ethyl-thio)acetoacetic acid methyl ester boiling at 129°–131° C./0.5 mm and prepared by alkylation of 2-acetoxy-ethanethiol with 4-chloro-acetoacetic acid methyl ester in a mixture of toluene and triethylamine.

Yield: (85%). Melting point: about 120° C.

Preparation 10: Compound 18

12.5 ml of concentrated hydrochloric acid was added dropwise to a solution of 26.8 g (0.1 mol) of Compound 17 in 100 ml of methanol. The reaction mixture was refluxed for 5 h. The precipitate was filtered with suction and recrystallized from water.

Yield: 11.5 g of Compound 18 (51%). Melting point: 199° C.

Preparation 11: Compound 20

Compound 20 was prepared analogously to Compound 6 as described above, but from 4-[2-(ethylthio)-ethylthio]-acetoacetic acid ethyl ester boiling at 140°–145° C./1 mm.

Yield: (25%). Melting point: about 170° C.

Preparation 12: Compound 21

15.3 g (0.1 mol) of 3-methylthiomethyl-5-amino-1,2,4-triazole and 16.2 g (0.1 mol) of 4-(methylthio)-acetoacetic acid methyl ester in 15 ml of acetic acid were refluxed for 24 h. The reaction product was concentrated by evaporation and purified by column chromatography.

Yield: 10 g (39%) of Compound 21. Melting point: 158° C.

Preparation 13: Compound 24

Compound 24 was prepared analogously to Compound 1 as described above, but from 2-(acetoxy-ethylthio)-acetoacetic acid ethyl ester boiling at 108°–110° C./0.5 mm and prepared by alkylation of 2-acetoxy-ethanethiol with 2-chloroacetoacetic acid ethyl ester in a mixture of toluene and triethylamine.

Yield: (77%). Melting point: about 100° C.

Preparation 14: Compound 25

Compound 25 was prepared analogously to Compound 18 as described above, but from Compound 24 as described above.

Yield: (67%). Melting point: about 210° C.

Preparation 15: Compound 30

15.4 g (0.05 mol)Aof 5-methyl-6-diethylaminomethyl-7-hydroxy-s-triazolo-[1,5-a]-pyrimidine prepared as described in the French patent specification No. 1,555,789 and 3.9 g (0.05 mol) of 2-mercapto-ethanol in 50 ml of dimethylformamide were heated for 16 h at 120° C. After filtration the reaction mixture was concentrated by evaporation. The residue was dissolved in 50 ml of water and acidified with concentrated hydrochloric acid. The precipitate was filtered with suction and rinsed with ethanol.

Yield: 6.5 g (54%) of Compound 30. Melting point: 170° C.

Preparation 16: Compound 31

12.4 g (0.1 mol) of methylthioacetyl chloride was added dropwise to 18.7 g (0.1 mol) of the sodium salt of 5-methyl-6-amino-7-hydroxy-s-triazolo-[1,5-a]-pyrimidine prepared as described in Chemical Abstracts 59, 1659e (1963) and 7.9 g (0.1 mol) of pyridine in 150 ml of anhydrous dioxan. The precipitate was filtered with suction, rinsed with dioxan, and purified by continuous extraction with methanol.

Yield: 10 g (40%) of Compound 31. Melting point: about 230° C.

It was surprising to find that substituted 7-hydroxy-s-triazolo-[1,5-a ]-pyrimidines corresponding to the above general formula, when added to silver halide emulsions of whatever type, yield unexpectedly improved fog-inhibition results without impairing the sensitivity and, when added to lith emulsions—even in the absence of cadmium salts—enhance their gradation and sharpen the toe portion of their characteristic curve.

Compounds according to the above general formula, which have a strong fog-inhibiting effect, are the following:

2-methylthiomethyl-5-methyl-7-hydroxy-s-triazolo-[1,5-a ]-pyrimidine (Compound 2);
2-carboxymethylthiomethyl-5-methyl-7-hydroxy-s-triazolo-[1,5-a ]-pyrimidine (Compound 4);
5-methylthiomethyl-7-hydroxy-s-triazolo-[1,5-a ]-pyrimidine (Compound 15);
5-methyl-6-hydroxyethylthio-7-hydroxy-s-triazolo-[1,5-a ]-pyrimidine (Compound 25).

Preferably, the compounds according to the above general formula are incorporated into the light-sensitive silver halide emulsion layer of a photographic element. The way in which the compounds are added to the light-sensitive silver halide emulsions is not critical and the addition can be made during any of the different steps of the emulsion preparation. For instance they can be added before, during, or after the emulsion has been sensitized chemically, preferably just before the coating of the emulsion on a suitable support such as e.g. paper, glass or film.

Instead of being incorporated into the light-sensitive silver halide emulsion layer, the novel compounds used in accordance with the invention can also be incorporated into another hydrophilic colloid layer of the photographic element (e.g. in an antistress or intermediate layer), which is in water-permeable relationship with the light-sensitive silver halide emulsion layer and coated at the same side of the support as said emulsion layer.

The compounds used in accordance with the present invention can be incorporated into any type of photographic element comprising a light-sensitive silver halide emulsion layer e.g. a spectrally sensitized silver halide emulsion layer, a non-spectrally sensitized silver halide emulsion layer, a silver halide emulsion layer of use in diffusion transfer reversal processes for the production of silver images, an X-ray silver halide emulsion layer, a lith silver halide emulsion layer, or a silver halide emulsion layer sensitive to infra-red radiation. They can be incorporated into high speed negative photographic elements as well as into rather low speed direct-positive elements. Various silver salts can be used as the light-sensitive silver salt e.g. silver bromide, silver iodide, silver chloride, or mixed silver halides e.g. silver chlorobromide, silver chlorobromoiodide, or silver bromoiodide.

The silver halides are dispersed in the common hydrophilic colloids such as gelatin, casein, zein, polyvinyl alcohol, carboxymethylcellulose, alginic acid, etc., gelatin being favoured, however.

The amount of 7-hydroxy-s-triazolo-[1,5-a ]-pyrimidine compounds used in accordance with the invention depends on the particular type of silver halide emulsion and the desired effect and may vary within very wide limits. The optimum amount is best determined by trial for each particular type of emulsion. In general, suitable concentrations are between 0.2 millimol and 30 millimol per mol of silver halide.

The light-sensitive silver halide emulsions can be sensitized chemically by effecting the ripening in the presence of small amounts of compounds containing sulphur e.g. allyl thiocyanate, allyl thiourea, sodium thiosulphate, etc. The emulsions can be sensitized also by means of reductors e.g. tin compounds as described in our U.K. patent specification No. 789,823 and small amounts of noble metal compounds e.g. gold, platinum, palladium, iridium, ruthenium, and rhodium.

Other additives such as hardening agents, wetting agents, plasticizers, colour couplers, developing agents, and spectral sensitizers can also be incorporated into the emulsion in the usual way.

The compounds according to the general formula can be used advantageously in combination with compounds that sensitize the emulsion by development acceleration e.g. alkylene oxide polymers. Such alkylene oxide polymers can be of various types. Various derivatives of alkylene oxides can be used to sensitize the silver halide emulsions e.g. alkylene oxide condensation products as described in the U.S. patent specification Nos. 2,531,832 and 2,533,990, in the U.K. patent specifications Nos. 920,637—940,051—945,340—991,608, and in Belgian patent specification No. 648,710. Other compounds that sensitize the emulsion by development acceleration and that are suitable for use in combination with the compounds according to the present invention are the onium derivatives of amino-N-oxides as described in the Belgian patent specification No. 686,520.

The stabilizers defined by the general formula herein can be used in combination with known stabilizers such as e.g. heterocyclic nitrogen containing thioxo compounds such as benzothiazoline-2-thione and 1-phenyl-Δ2-tetrazoline-5-thione, with mercury compounds such as those described in the Belgian patent specification Nos. 524,121—677,337—707,386—709,195 and, of course, also in conjunction with known compounds of the hydroxytriazolopyrimidine type.

In lith emulsions one or more compounds corresponding to the above general formula can be used alone or in combination with other additives that increase the sensitivity. A lith silver halide emulsion comprises at least 50 mol% of chloride and not more than 5% of iodide, the remainder being bromide. Preferably, lith emulsions contain at least 60 mol% of chloride, not more than 40 mol% of bromide and not more than 5 mol% of iodide.

Photographic lith-type elements that may contain compounds corresponding to the above general formula can be ortho or pan sensitive or sensitive to any other desired spectral region and lith-type elements incorporating said compounds can be used for any application for which lith-type elements are customarily employed e.g. for the reproduction of continuous tone photographs or line drawings for the preparation of printing plates.

In the following examples the effects of some of the compounds corresponding to the above general formula in photographic silver halide emulsions are illustrated.

EXAMPLE 1

A photographic gelatin silver chloride emulsion having an average grain diameter of 260 nm was digested in the presence of gold and thiosulphate until it reached its maximum speed. The emulsion obtained was divided into four portions, to each portion of which 1 millimol of antifoggant as listed in Table 2 hereinafter was added per 100 g of silver nitrate. Each of the emulsion samples thus obtained was coated on a conventional support and dried.

The freshly prepared samples were developed at 20° C. for 3 min. in a developing solution having the following composition:

| water | 800 ml |
|---|---|
| p-monomethylaminophenol sulphate | 1.5 g |
| anhydrous sodium sulphite | 50 g |
| hydroquinone | 6 g |
| anhydrous sodium carbonate | 32 g |
| potassium bromide | 2 g |
| water to make | 1000 ml |

The values of fog and speed are listed also in Table 2. The density (D) values given for fog are absolute values. The values of speed were measured at density (D) 1.0 above fog. The sample comprising compound A was given the speed value 100, the values obtained with the samples comprising other compounds being percent values relating to the value of the sample containing compound A.

Compound A is a comparison antifoggant disclosed in Example 1 of the U.S. patent specification No. 2,566,659; it carries a methylthio function in the 2-position and a methyl group in the 5-position of a 7-hydroxy-s-triazolo-[1,5-a]-pyrimidine ring system.

Compound B is a comparison antifoggant disclosed in the U.K. patent specification No. 1,500,278; it carries a carboxymethylthio function in the 2-position and a methyl group in the 5-position of a 7-hydroxy-s-triazolo-[1,5-a]-pyrimidine ring system.

TABLE 2

| Antifoggant added | Fog | Speed |
|---|---|---|
| Compound A (comparison) | 0.09 | 100 |
| Compound B (comparison) | 0.07 | 85 |
| Compound 2 | 0.04 | 102 |
| Compound 15 | 0.03 | 141 |

Comparison of the above results shows that the fog-inhibiting effect of the compounds 2 and 15 of the invention is manifestly stronger than that of the known compounds A and B. It also shows that the speed obtained with the compounds 2 and 15 of the invention at least equals, and in fact, exceeds the speed obtained with the comparison compounds A and B.

EXAMPLE 2

A conventional photographic gelatin silver bromoiodide emulsion (4.5 mol% iodide) comprising an amount of silver halide equivalent to 50 g of silver nitrate per kg of emulsion was divided into aliquot portions. To all but one portion an antifoggant was added in the amounts indicated in Table 3 hereinafter (in millimol per 50 g of silver nitrate). Each of the emulsion samples thus obtained was coated on a conventional support and dried.

The values of fog and speed of these emulsion samples were determined shortly after preparation and again after incubation for 5 days at 57° C. and 34 percent relative humidity.

Development occurred at 20° C. for 5 min. in a developing solution having the same composition as that described in Example 1.

The values of fog and speed obtained are listed in Table 3. The density (D) values given for fog are absolute values. The values I and II given for the speed are relative values, "Speed I" standing for speed values measured at density (D) 0.1 above fog and "Speed II" standing for speed values measured at density (D) 1.0 above fog. The emulsion sample comprising 0.5 millimol of compound C was given a speed value of 100, the speed values of the other emulsion samples being percent values relating to the value of this reference sample.

Compound C (comparison compound) is the conventionally used 5-methyl-7-hydroxy-s-triazolo-[1,5-a]-pyrimidine.

Compound B (comparison compound) corresponds with Compound B in Example 1.

TABLE 3

| Antifoggant added | Concentration in millimol | Fresh emulsion | | | Incubated emulsion | | |
|---|---|---|---|---|---|---|---|
| | | Fog | Speed I | Speed II | Fog | Speed I | Speed II |
| none | — | 0.21 | 126 | 117 | 2.29 | 06 | |
| Compound C | 0.5 | 0.08 | 100 | 100 | 1.60 | 21 | * |
| Compound C | 1.0 | 0.08 | 83 | 95 | 1.13 | 54 | 15 |
| Compound B | 0.5 | 0.12 | 115 | 126 | 2.20 | 07 | * |
| Compound B | 1.0 | 0.09 | 102 | 123 | 1.84 | 20 | * |
| Compound 4 | 0.5 | 0.06 | 45 | 60 | 0.83 | 56 | 25 |
| Compound 4 | 1.0 | 0.06 | 29 | 44 | 0.42 | 61 | 58 |
| Compound 25 | 1.0 | 0.05 | 70 | 66 | 0.86 | 110 | 37 |
| Compound 25 | 2.0 | 0.06 | 58 | 66 | 0.43 | 129 | 98 |

*In this case Speed II cannot be determined because the fog is too high.

Comparison of the above results shows that the fog-inhibiting effect of the compounds 4 and 25 of the invention is considerably stronger than that of the known compounds C and B. It also shows that the speed after incubation in the case of the comparison compounds C and B dropped steeply, and in general rose slightly in the case of compounds 4 and 25 of the invention, thus demonstrating that the addition of the compounds of the invention does not result in a reduction of the speed but rather in a stabilization thereof.

EXAMPLE 3

A lith-type gelatin silver chlorobromoiodide emulsion (8.6 mol% chloride, 16.0 mol% bromide, and 0.4 mol% iodide) having an average grain diameter of 330 nm was digested in the presence of gold, thiosulphate, and p-toluene-thiosulphonic acid until it reached its maximum speed. The emulsion obtained wad divided into four portions, to each portion of which 1.0 millimol of compound as listed in Table 4 hereinafter was added per 100 g of silver nitrate. Each of the emulsion samples thus obtained was coated on a conventional support and dried.

The freshly prepared samples were developed for 1 min 45 s at 27° C. in a developing solution comprising 1 part of composition A, 0.5 part of composition B, and 2.5 parts of demineralized water:

| Composition A | |
|---|---|
| tetrasodium salt of ethylene diamine tetraacetic acid | 4 g |
| boric acid | 24 g |
| anhydrous potassium carbonate | 280 g |
| sodium salt of formaldehyde hydrogen sulphite | 200 g |
| potassium metabisulphite | 15 g |
| potassium bromide | 8 g |
| potassium chloride | 24 g |
| demineralized water to make | 1000 ml |
| Composition B | |
| potassium metabisulphite | 2 g |
| hydroquinone | 60 g |

| -continued | |
|---|---|
| potassium hydroquinone sulphonate | 40 g |
| polyethylene glycol (1000) | 1 g |
| triethylene glycol | 125 ml |
| demineralized water to make | 500 ml |

The values of fog, speed, and gradation are listed in Table 4. The density (D) values given for fog are absolute values. The values of speed were measured at density (D) 1.30 above fog. The values of gradation are the values of gamma between 0.04 and 1.30 of the characteristic curve. (D) 0.04 corresponds with 5% of dot area upon screen exposure and (D) 1.30 corresponds with 95% of dot area.

The sample containing compound B was given the speed value 100, the values obtained with the samples containing the other compounds being percent values relating to the value of the sample containing compound B.

Compound B and Compound A (both comparison compounds) are the same as Compounds B and A in Example 1.

TABLE 4

| Compound added | Fog | Speed | Gradation |
|---|---|---|---|
| Compound B (comparison) | 0.02 | 100 | 1.15 |
| Compound A (comparison) | 0.01 | 162 | 1.00 |
| Compound 15 | 0.02 | 282 | 2.05 |
| Compound 2 | 0.02 | 102 | 1.34 |

Comparison of the above results shows that the gradation obtained with a lithographic silver halide emulsion comprising the compounds 2 and 15 of the invention is higher than that obtained with the known compounds B and A.

We claim:

1. Photographic element comprising a support and at least one light-sensitive silver halide emulsion layer and comprising in said emulsion layer and/or in at least one water-permeable hydrophilic colloid layer coated at the same side of the support as said emulsion layer at least one 7-hydroxy-s-triazoloe-[1,5-a]-pyrimidine, wherein said 7-hydroxy-s-triazolo-[1,5-a]-pyrimidine corresponds to the following general formula:

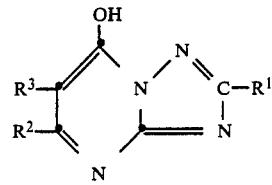

wherein:
each of $R^1$, $R^2$, and $R^3$, which may be the same or different, represents:
hydrogen,
a $C_1$–$C_8$ alkyl group, or
an $Alk_1$—X—$Alk_2$—Y—group, wherein
$Alk_1$ represents a $C_1$–$C_8$alkyl group or a substituted $C_1$–$C_8$alkyl group,
Y represents a single bond, —O—, —S—, —COHN—, —SO$_2$NH—, or —NHCONH—,
X represents —S—, and when Y is not a single bond, X can also represent —O—, and
$Alk_2$ represents a $C_1$–$C_8$alkylene group or a substituted $C_1$–$C_8$alkylene group,
$R^3$ can alternatively represent a $C_1$–$C_8$alkyl-thio group or a $C_1$–$C_8$alkyl-thio group, the $C_1$–$C_8$alkyl of which can be substituted,
at least one of $R^1$, $R^2$, and $R^3$, however, being other than hydrogen and other than $C_1$–$C_8$alkyl said 7-hydroxy-s-triazolo-[1,5-a]-pyrimidine being present in an amount sufficient to provide improved stabilization.

2. A photographic element according to claim 1, wherein $R^1$ in said 7-hydroxy-s-triazolo-[1,5-a]-pyrimidine is methylthiomethyl, $R^2$ is methyl, and $R^3$ is hydrogen.

3. A photographic element according to claim 1, wherein $R^2$ in said 7-hydroxy-s-triazolo-[1,5-a]-pyrimidine is methylthiomethyl and each of $R^1$ and $R^3$ is hydrogen.

4. A photographic element according to claim 1, wherein $R^1$ in said 7-hydroxy-s-triazolo-[1,5-a]-pyrimidine is carboxymethylthiomethyl, $R^2$ is methyl, and $R^3$ is hydrogen.

5. A photographic element according to claim 1, wherein $R^2$ in said 7-hydroxy-s-triazolo-[1,5-a]-pyrimidine is methyl, $R^3$ is 2-hydroxy-ethylthio, and $R^1$ is hydrogen.

6. A photographic element according to claim 1, wherein said 7-hydroxy-s-triazolo-[1,5-a]-pyrimidine compound is present in said light-sensitive silver halide emulsion layer in an amount ranging from 0.2 to 30 millimol per mol of silver halide.

7. A photographic element according to claim 1, wherein said light-sensitive silver halide emulsion layer is a lith-type silver halide emulsion layer.

* * * * *